United States Patent
Tang et al.

(10) Patent No.: US 11,754,498 B2
(45) Date of Patent: Sep. 12, 2023

(54) SINGLE AIEGEN FOR MULTIPLE TASKS: IMAGING OF DUAL ORGANELLES AND EVALUATION OF CELL VIABILITY

(71) Applicant: THE HONG KONG UNIVERSITY OF SCIENCE AND TECHNOLOGY, Hong Kong (CN)

(72) Inventors: Benzhong Tang, Hong Kong (CN); Ruoyao Zhang, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 266 days.

(21) Appl. No.: 17/066,655

(22) Filed: Oct. 9, 2020

(65) Prior Publication Data
US 2021/0109024 A1 Apr. 15, 2021

Related U.S. Application Data

(60) Provisional application No. 62/973,552, filed on Oct. 11, 2019.

(51) Int. Cl.
*G01N 33/58* (2006.01)
*G01N 21/64* (2006.01)
*C07D 215/12* (2006.01)
*C12Q 1/44* (2006.01)

(52) U.S. Cl.
CPC ....... *G01N 21/6428* (2013.01); *C07D 215/12* (2013.01); *C12Q 1/44* (2013.01); *G01N 33/582* (2013.01); *G01N 2021/6439* (2013.01)

(58) Field of Classification Search
CPC .... G01N 21/6428; G01N 33/582; C12Q 1/44; C07D 215/12
See application file for complete search history.

(56) References Cited

PUBLICATIONS

Gu et al., ACS Appl. Bio Mater., 2019, 2:3120-3127.*

* cited by examiner

*Primary Examiner* — Bin Shen
(74) *Attorney, Agent, or Firm* — Nath, Goldberg & Meyer; Joshua B. Goldberg

(57) ABSTRACT

A fluorescent probe can include a compound exhibiting aggregation-induced emission (AIE). The probe can be used for selectively staining mitochondria and lipid droplets and detecting esterase activity. The probe includes an acetoxyl group which can be recognized by esterase in an esterase activity assay. As enzyme activity can reflect cell viability, the probe can be useful in cell viability detection. In addition, the probe includes a cationic moiety to target mitochondria and a lipophilic moiety that can target lipid droplets. A calculated log P value of the lipophilic moiety can be larger than 5.

19 Claims, 15 Drawing Sheets

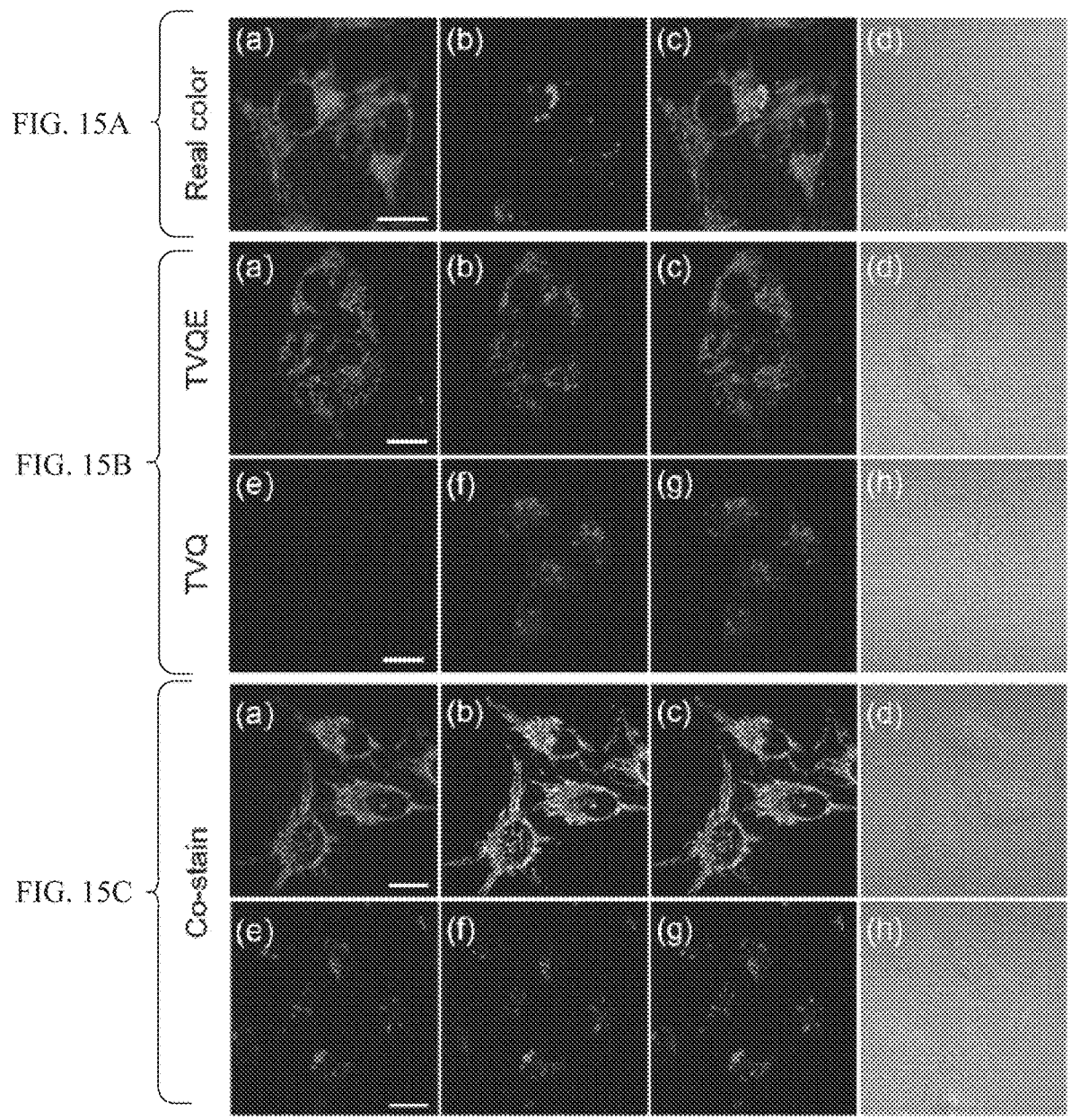

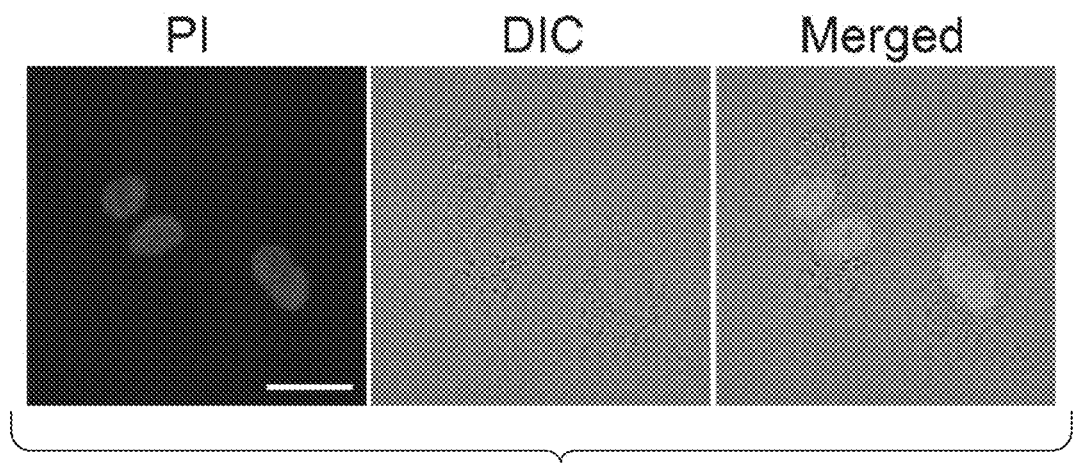
FIG. 19
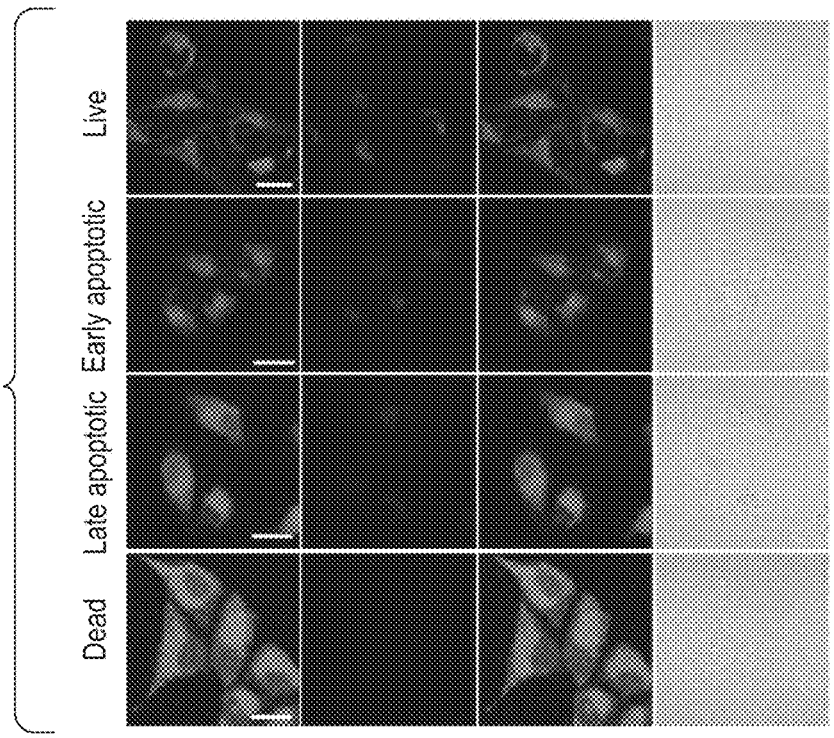
FIG. 20A
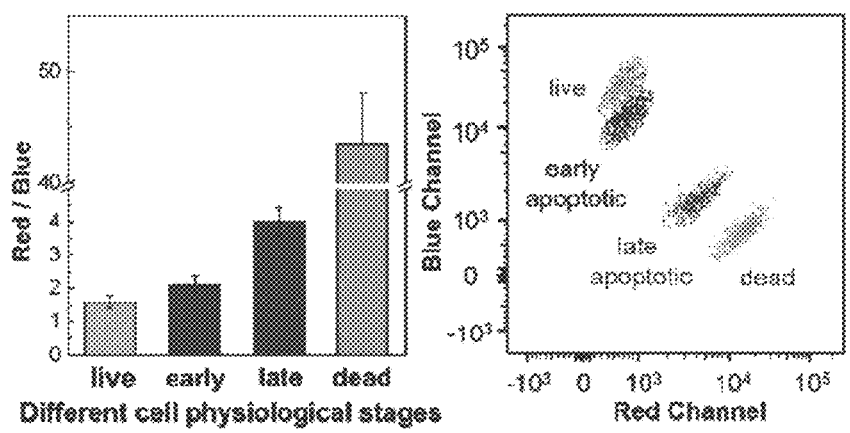
FIG. 20B
FIG. 20C

SINGLE AIEGEN FOR MULTIPLE TASKS: IMAGING OF DUAL ORGANELLES AND EVALUATION OF CELL VIABILITY

CROSS-REFERENCE

The present application claims priority to U.S. Provisional Patent Application No. 62/973,552, filed Oct. 11, 2019, which was filed by the inventors hereof and is incorporated herein by reference in its entirety.

FIELD

The present subject matter relates generally to fluorescent probes for identifying multiple organelles and detecting cell viability.

BACKGROUND

A cell, the basic unit of life, is a sophisticated chemical machine that performs various biological activities. Inside a cell, various species, including small biomolecules and macromolecules, collaborate to perform multiple biological functions. For example, enzymes, one of the most important intracellular macromolecules, catalyze a vast range of reactions essential to normal life. Organelles, such as mitochondria and lipid droplets, are indispensable for all kinds of biological processes. Amongst other functions, mitochondria provide continuous energy and regulate cellular status. Lipid droplets are involved in lipid metabolism, energy storage, and membrane synthesis.

The interplay among various chemical species and different organelles plays a central role in significant biological events. For example, cell apoptosis is triggered by the increase of mitochondrial membrane permeability, which releases cytochromes into the cytoplasm and induces the activation of caspases 3/7. This process is also accompanied by a decrease of enzymatic activity and a decrease in cell viability. Lipid droplets can collect toxic acids to reduce inflammation reactions. Therefore, fully understanding the complicated interplay among various chemical species and organelles is important to unravel the mysteries of cellular function.

In recent years, researchers have developed many imaging methods to visualize chemical species and organelles inside a cell. Among these methods, fluorescence microscopy has become a powerful tool due to its high selectivity and sensitivity. Fluorescent probes that can selectively image one chemical species or one organelle have been widely developed. For example, a ratiometric fluorophore has been developed for sensing intracellular esterase. MitoTracker probes and Nile Red have been developed for visualizing mitochondria and lipid droplets, respectively. Notably, some fluorescent probes for dual imaging tasks have been also reported. For instance, Tang et al. reported a fluorescent nanoprobe for visualization of epithelial mesenchymal transition and apoptosis processes.

Aggregation-induced emission (AIE) materials display unique advantages in bioimaging applications. Conventional fluorophores, such as rhodamine, are often used in low concentrations due to aggregation-caused quenching (ACQ) effects in high concentrations. This ACQ effect limits the use of many conventional fluorophores in bioimaging because they are easily photobleached. Unlike ACQ fluorophores, isolated AIE luminogens (AIEgens) in dilute solution emit weak emission or no emission at all. However, the restriction of intramolecular motion (RIM) in aggregation status or high-viscosity conditions can dramatically enhance fluorescence. Consequently, AIEgens are greatly favorable for imaging high-viscosity organelles or species in cytoplasm with high fidelity.

Recently, a variety of AIEgens with good biocompatibility and high photostability have been developed for imaging chemical species and organelles, respectively. For example, an AIEgen named DEAM with an esterase recognizable acetoxyl group was found to be useful for an esterase activity assay. In addition, based on a large mitochondrial membrane potential (MMP), some AIEgens with cationic moiety have been designed. The electrostatic interaction between the cationic moiety and MMP effectively drives the AIEgens to mitochondria. As lipid droplets have an inherent lipophilic environment, some reported lipophilic AIEgens, such as 6-(1H-indol-1-yl)-2-phenyl-9-propyl-9H-purine or "AIP," have been developed for specific imaging of lipid droplets. However, most of the reported AIEgens can only selectively image one kind of chemical species or one organelle.

SUMMARY

The present subject matter relates to a fluorescent AIE probe that can be used for selectively staining mitochondria and lipid droplets as well as for detecting esterase activity. The probe includes a cationic moiety to target mitochondria and a lipophilic moiety that can target lipid droplets. In addition, the probe includes an acetoxyl group which can be recognized by esterase in an esterase activity assay. As enzyme activity can reflect cell viability, the probe can be useful in cell viability detection. A calculated log P value of the lipophilic moiety can be larger than 5.

In an embodiment, the fluorescent probe comprises a compound having the following structural formula:

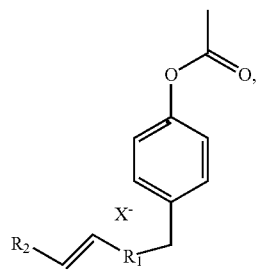

wherein $X^-$ is selected from the group consisting of $Br^-$, $I^-$, $PF_6^-$, and $ClO_4^-$;

$R_1$ is selected from the group consisting of

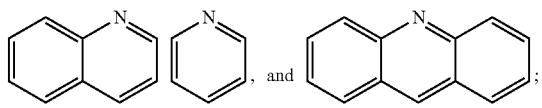

and $R_2$ is selected from the group consisting of

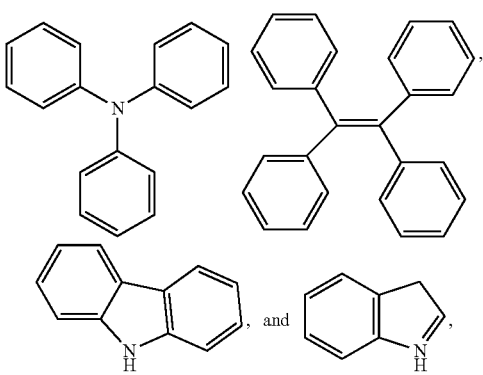

In an embodiment, the fluorescent probe comprises the following compound:

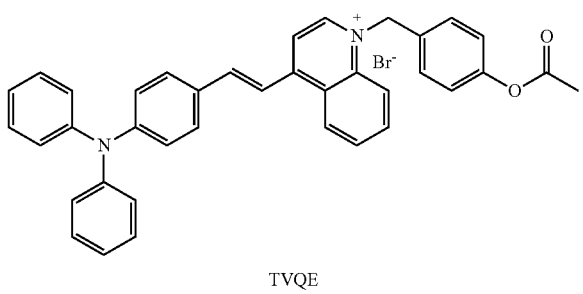

TVQE

A method of cellular imaging can include contacting a target cell with the fluorescent probe and identifying at least one cellular target of interest using an imaging method. In an embodiment, the cellular target of interest can include at least one of a mitochondrion and a lipid droplet.

A method of determining viability of a cell can include contacting a target cell with the fluorescent probe and detecting esterase activity using an imaging method. A change of emission from red to blue can indicate hydrolyzing of the compound by esterase and an intensity ratio of a red emission and a blue emission can indicate viability of the target cell.

BRIEF DESCRIPTION OF DRAWINGS

Various embodiments will now be described in detail with reference to the accompanying drawings.

(FIG. 11B) plots of relative FL emission intensity versus the composition of the EtOH/Hexane mixtures and FL maximum of TVQE; (FIG. 11C) normalized FL spectra of TVQE (solid line) and TVQ (dashed line) in different solvents; and (FIG. 11D) FL spectra of TVQE with esterase (1 U/mL) at different time. λex=405 nm.

(FIG. 12B) normalized absorption and FL spectra of TVQ in PBS; (FIG. 12C) FL spectrum of TVQE in solid state. λex=500 nm; and (FIG. 12D) FL spectra of TVQE with esterase (1 U/mL) at different time. λex=530 nm.

FIGS. 15A-15C depict (FIG. 15A) images of live HeLa cells stained with 2 μM TVQE. (a): λex=488 nm, λem=550-750 nm; (b): λex=405 nm, λem=420-600 nm; (FIG. 15B) CLSM images of live HeLa cells stained with 2 μM TVQE and TVQ. (a) and (e): λex=488 nm, λem=550-700 nm; (b) and (f): λex=405 nm, λem=420-550 nm; (FIG. 15C) CLSM images of live HeLa cells stained with 2 μM TVQE (a, e), 0.2 μM MTDR (b), and 1 μM Nile Red (f). (a): λex=488 nm, λem=550-700 nm; (b): λex=640 nm, λem=650-700 nm; (e): λex=405 nm, λem=420-520 nm; (f): λex=561 nm, λem=570-600 nm. (all (c) and (g) panels reflect merged images; all (d) and (h) panels reflect DIC images; scale bar=20 μm).

(FIG. 17B) fluorescence intensity changes in red and blue channel, and blue/red intensity ratio during the process that TVQE stained live HeLa cells.

FIG. 19 depicts CLSM images of live HeLa cells treated with 10 mM H$_2$O$_2$ for 4.5 h and stained 1 μM PI for 20 min. λex=488 nm, λem=600-700 nm. Scale bar=20 μm.

FIGS. 20A-20C depict (FIG. 20A) CLSM images of live, early apoptotic, early apoptotic, and dead HeLa cells stained with 2 μM TVQE; blue channel: λex=405 nm, λem=420-550 nm; red channel: λex=488 nm, λem=550-700 nm. Scale bar=20 μm; (FIG. 20B) the relevant intensity ratio of red and blue channel in A; and (FIG. 20C) statistical analysis of live, early apoptotic, late apoptotic, and dead cells stained by TVQE by flow cytometry. Blue channel: λex=405 nm, λem=430-470 nm; Red channel: λex=488 nm, λem=675-715 nm.

DETAILED DESCRIPTION

Figure 1:
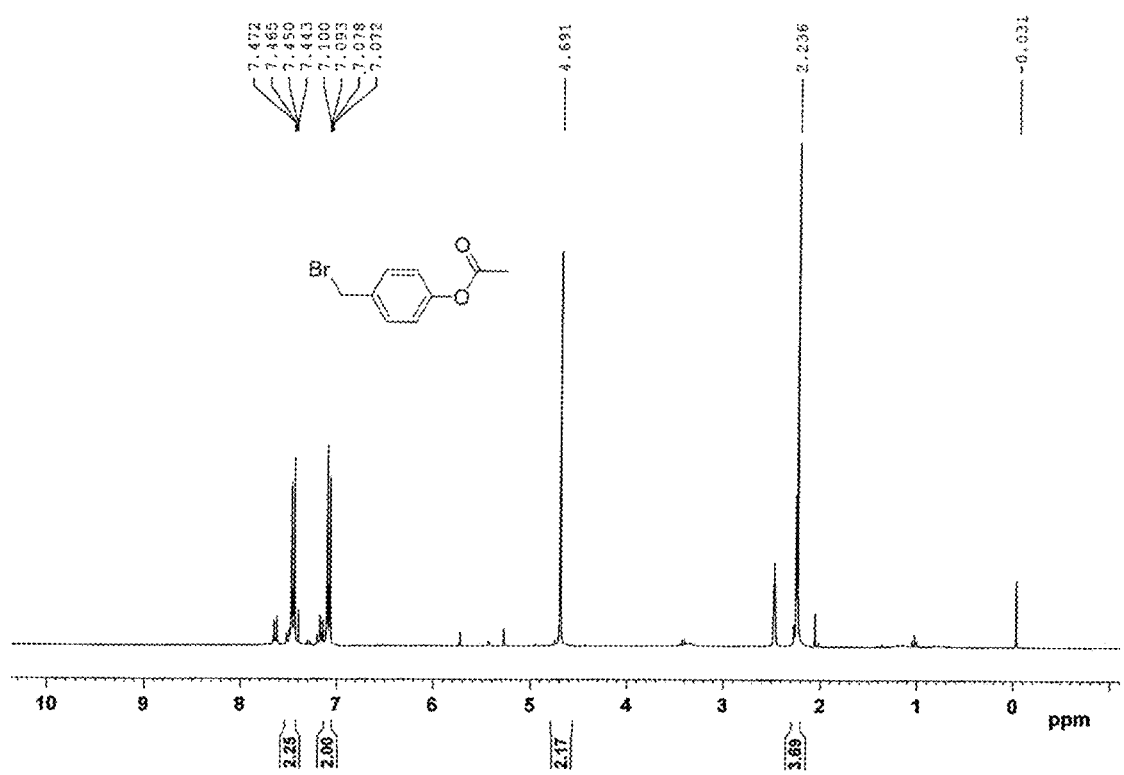
FIG. 1 depicts the $^1$H NMR spectrum of compound 2 in DMSO-$d_6$.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, 5 to 22 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

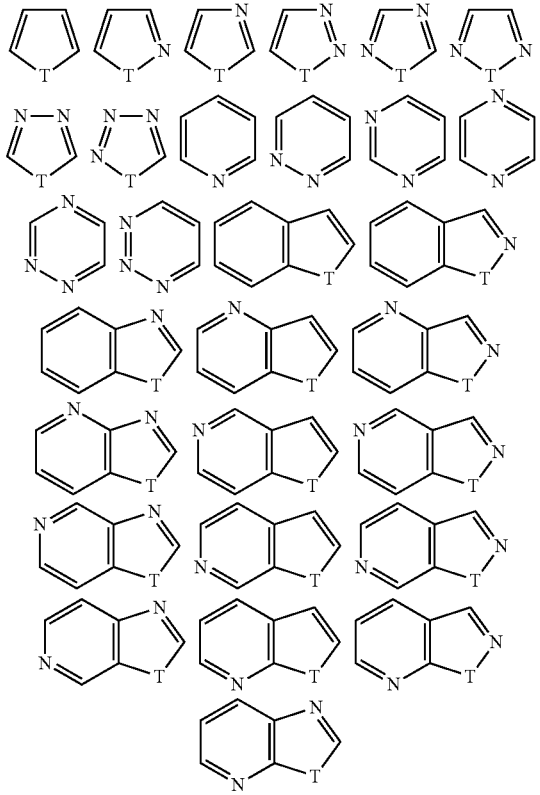

where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinox-alyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Fluorescent Probes

The present subject matter relates to a fluorescent probe that includes a compound exhibiting aggregation-induced emission (AIE).

In an embodiment, the fluorescent probe comprises a compound having the following structural formula:

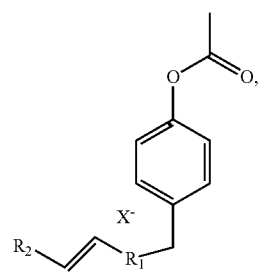

wherein X⁻ is selected from the group consisting of Br⁻, I⁻, PF$_6^-$, and ClO$_4^-$;

R$_1$ is selected from the group consisting of

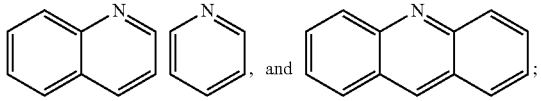

and

R$_2$ is selected from the group consisting of

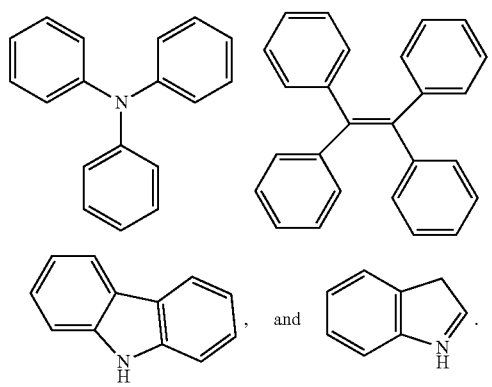

In an embodiment, the fluorescent probe comprises the following compound:

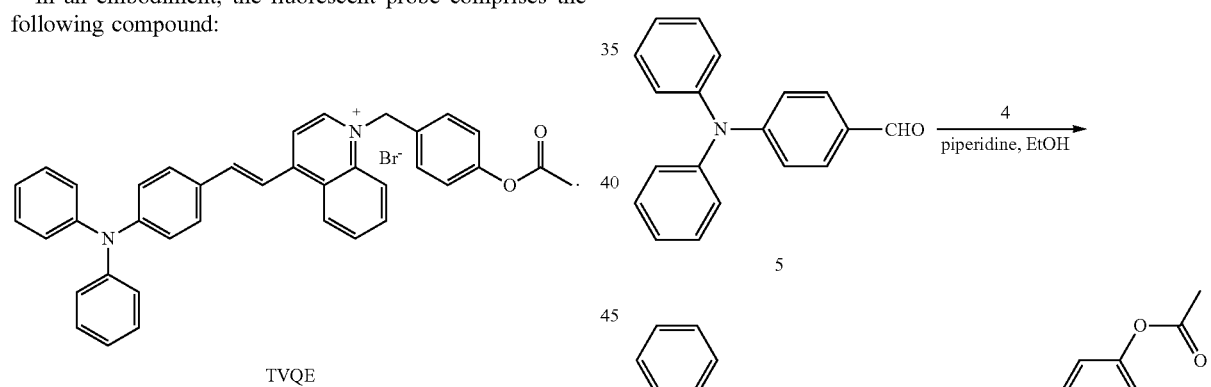

TVQE

The compound, also referred to herein as "TVQE", includes a cationic moiety to target mitochondria and a lipophilic moiety that can target lipid droplets. The compound also includes an acetoxyl group which can be recognized by esterase in an esterase activity assay. Once contacted with a cell, the compound first targets mitochondria and emits red fluorescence. Then, the compound is partially hydrolyzed by esterase to a lipophilic compound, also referred to herein as "TVQ", that emits blue fluorescence and accumulates in lipid droplets. As such, the probe can be used for selectively staining mitochondria and lipid droplets as well as for detecting esterase activity. As enzyme activity can reflect cell viability, the probe can be useful in cell viability detection. The lipophilic compound, TVQ, can have a high lipophilicity. A calculated log P value of TVQ can be larger than 5. For example, the calculated log P value of TVQ can be 8.314.

An exemplary reaction scheme for preparing TVQE and TVQ is provided below:

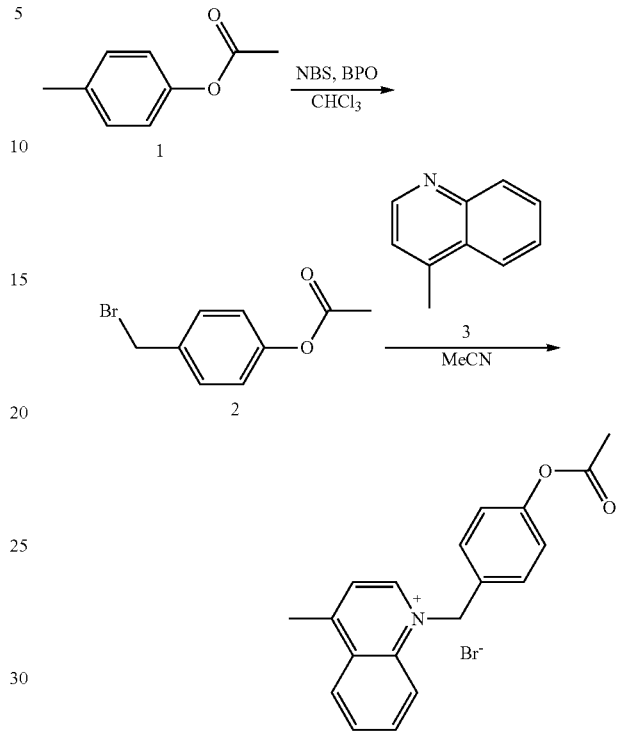

-continued

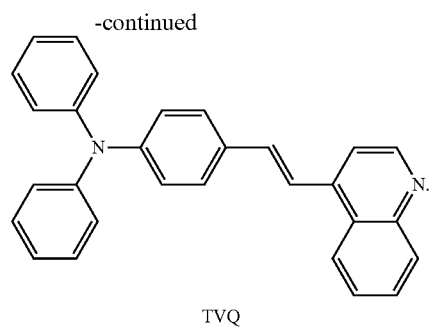

TVQ

Organelle Staining and Enzyme Activity Detection

The compound can provide distinct emission color changes in aqueous environment from red to blue after hydrolysis by esterase. Live cell imaging experiments, described in detail herein, reveal that the compound first targets mitochondria and emits red fluorescence. Then, the compound is partially hydrolyzed by esterase to a lipophilic compound, "TVQ", that emits blue fluorescence and accumulates in lipid droplets.

In an embodiment, a method of cellular imaging can include contacting a target cell with TVQE and identifying at least one cellular target of interest using an imaging method. The imaging method can include at least one of fluorescence microscopy and confocal laser scanning microscopy. In an embodiment, the target cell is a live cell. In an embodiment, the target cell is a cancer cell. In an embodiment, the target of interest includes at least one of a mitochondrion and a lipid droplet. In an embodiment, the target of interest includes a mitochondrion and a lipid droplet.

An intensity of a red and blue emission can indicate a cell viability or physiological stage of a cell, as esterase activity varies in different cell physiological stages. As such, TVQE can be used to qualitatively and statistically differentiate live, early apoptotic, late apoptotic and dead cells. Further, TVQE can be used in phototherapy to evaluate the activity and performance of photosensitizers and drugs based on a determined cell viability.

In an embodiment, a method of determining viability of a cell can include contacting a target cell with TVQE and detecting esterase activity using an imaging method. The esterase activity can be detected upon a change of emission from red to blue. The change of emission from red to blue indicates hydrolysis of the compound by esterase. An intensity ratio of a red emission and a blue emission indicates viability of the target cell. The imaging method can be selected from fluorescence microscopy and confocal laser scanning microscopy. The target cell can be a cancer cell. An intensity ratio of the red and blue emission indicates a cell state selected from the group consisting of live, early, apoptotic, late apoptotic, and dead. The intensity ratios can be quantified by flow cytometry.

The present teachings are illustrated by the following examples.

EXAMPLES

Example 1

Synthesis and Characterization of Representative Compounds

Synthesis of Compound 2

N-Bromosuccinimide (NB S) (3.11 g, 17.5 mmol), compound 1 (2.49 g, 16.6 mmol), and dibenzoyl peroxide (BPO) (0.80 g, 3.3 mmol) were dissolved in $CHCl_3$ (20 mL) and the mixture was stirred at 61° C. for 4 h. Then, the mixture was cooled to room temperature. After filtration, $CHCl_3$ was removed under reduced pressure. Then, the residue was purified by flash chromatography to give compound 2 as a white solid (2.52 g, 66%). $^1$H NMR (300 MHz, DMSO-$d_6$), δ (ppm): 7.44-7.47 (m, 2H), 7.07-7.10 (m, 2H), 4.69 (s, 2H), 2.24 (s, 3H) FIG. 1).

Synthesis of Compound 4

Figure 2:
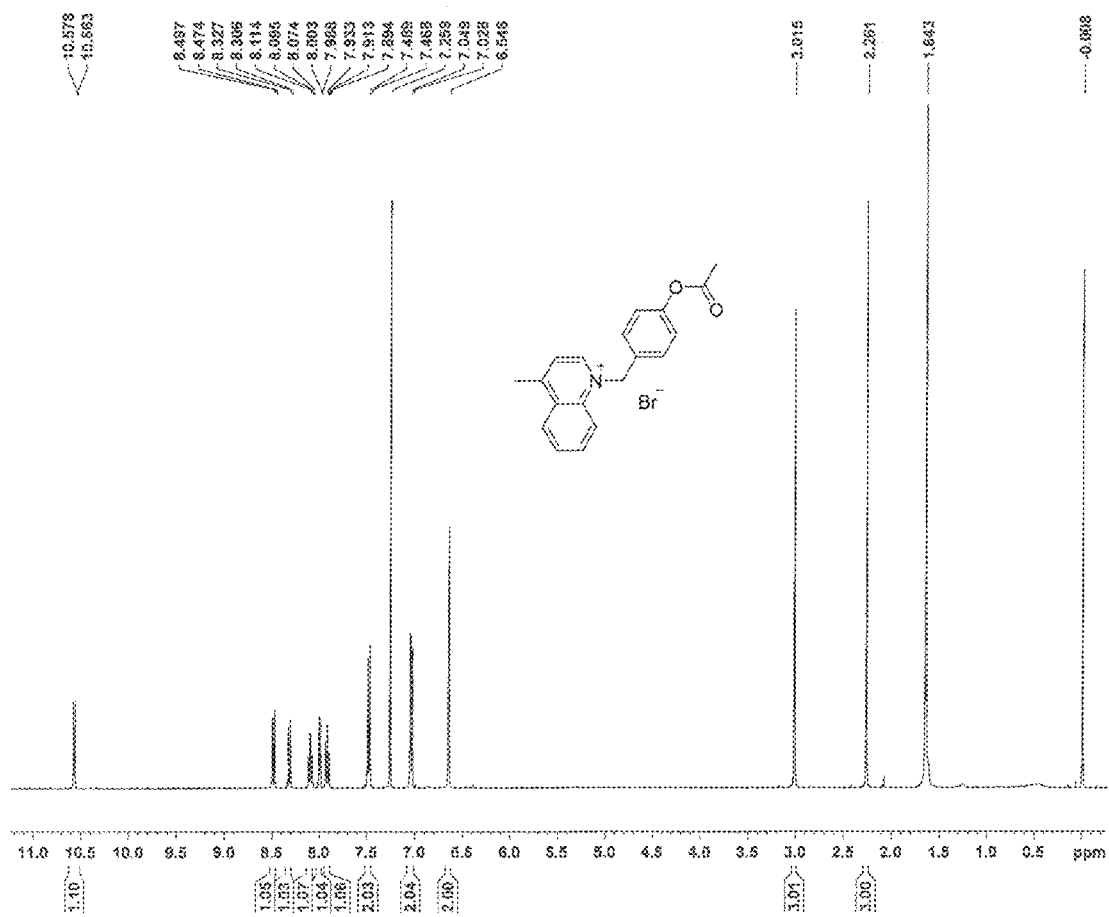
FIG. 2 depicts the $^1$H NMR spectrum of compound 4 in CDCl$_3$.

Compound 2 (1.15 g, 5 mmol) and compound 3 (0.72 g, 5 mmol) were dissolved in MeCN and stirred at room temperature for 24 h. Then, the mixture was poured into petroleum ether and the gray white solid was filtrated. After recrystallization, compound 4 was obtained as a gray white solid (0.96 g, 52%). $^1$H NMR (400 MHz, $CDCl_3$), δ (ppm): 10.57 (d, J=6.00 Hz, 1H), 8.49 (d, J=9.20 Hz, 1H), 8.32 (d, J=8.40 Hz, 1H), 8.09 (t, J=8.00 Hz, 1H), 8.00 (d, J=6.00 Hz, 1H), 7.91 (t, J=7.80 Hz, 1H), 7.48 (d, J=8.40 Hz, 2H), 7.04 (d, J=8.40 Hz, 2H), 6.65 (s, 2H), 3.02 (s, 3H), 2.26 (s, 3H) (FIG. 2).

Synthesis of Compound TVQE

Figure 3:
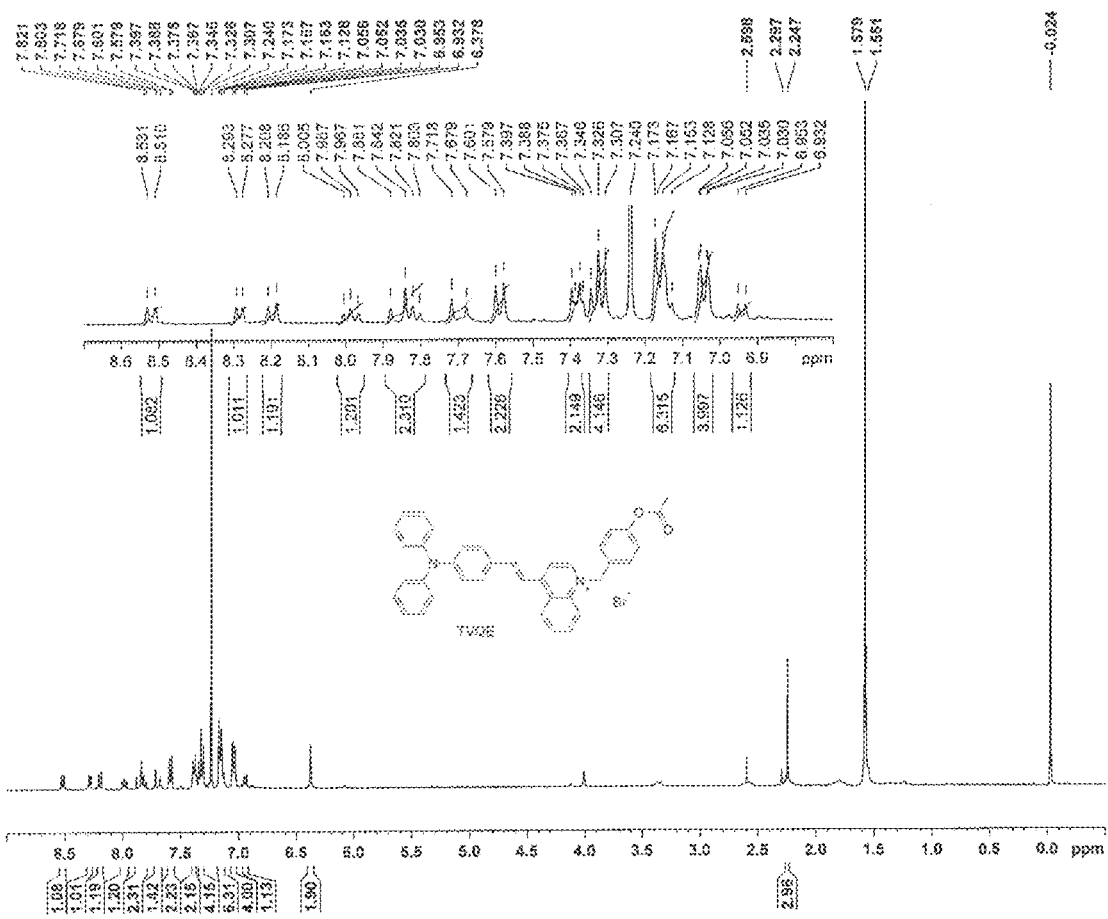
FIG. 3 depicts the $^1$H NMR spectrum of TVQE in CDCl$_3$.
Figure 4:
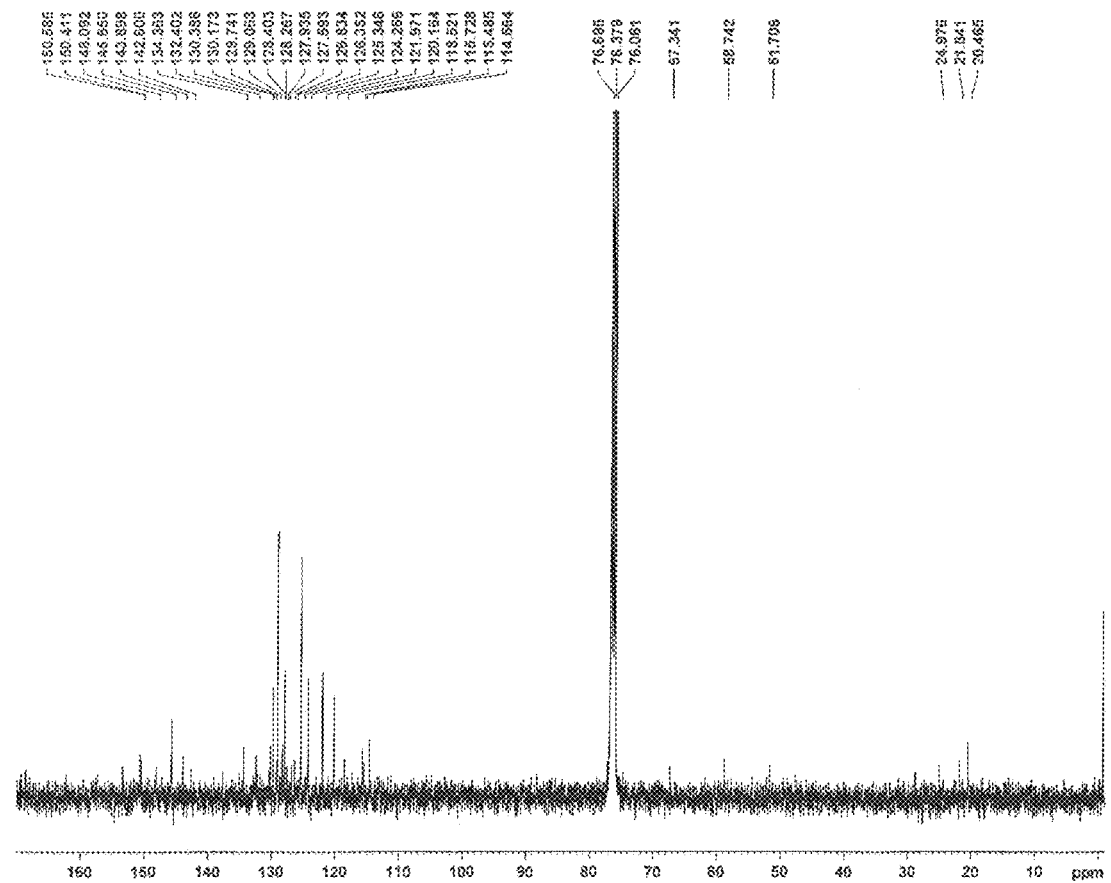
FIG. 4 depicts the $^{13}$C NMR spectrum of TVQE in CDCl$_3$.
Figure 5:
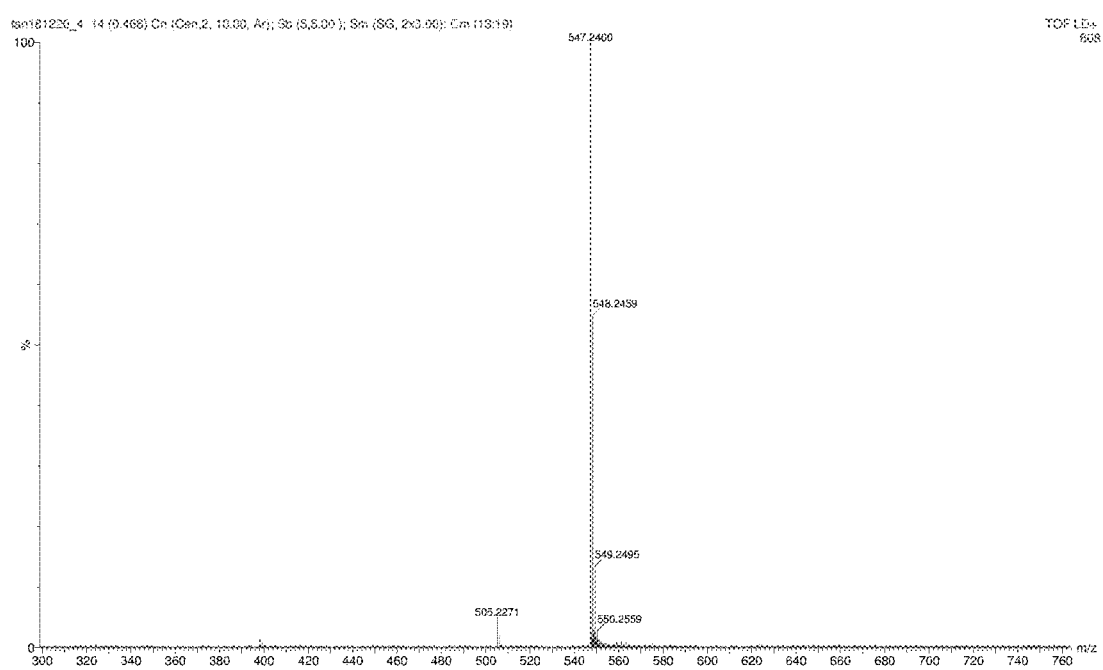
FIG. 5 depicts the HRMS of TVQE.

Compound 4 (0.37 g, 1 mmol) and compound 5 (0.27 g, 1 mmol) were dissolved in ethanol (30 mL) and stirred with addition of piperidine (200 μL). The mixture was stirred at 78° C. for 4 h. Then, the mixture was cooled to room temperature, poured into petroleum ether, and extracted with $CH_2Cl_2$. After $CH_2Cl_2$ was removed under reduced pressure, the residue was purified by flash chromatography to give TVQE as a dark purple solid (0.11 g, 17%). $^1$H NMR (400 MHz, $CDCl_3$), δ (ppm): 8.52 (d, J=8.40 Hz, 1H), 8.29 (d, J=6.40 Hz, 1H), 8.20 (d, J=8.80 Hz, 1H), 7.99 (t, J=7.60 Hz, 1H), 7.80-7.88 (m, 2H), 7.70 (d, J=15.6 Hz, 1H), 7.59 (d, J=8.8 Hz, 2H), 7.37-7.40 (m, 2H), 7.33 (t, J=7.8 Hz, 4H), 7.13-7.17 (m, 6H), 7.03-7.06 (m, 4H), 6.94 (d, J=8.4 Hz, 1H), 6.38 (s, 2H), 2.25 (s, 3H) (FIG. 3). $^{13}$C NMR (400 MHz, $CDCl_3$), δ (ppm): 148.09, 145.65, 143.90, 134.36, 132.40, 130.39, 130.17, 129.74, 129.06, 128.40, 128.27, 127.94, 127.59, 126.83, 126.35, 125.35, 124.26, 121.97, 120.16, 118.52, 115.73, 115.49, 114.56, 67.34, 58.74, 51.71, 24.98, 21.84, 20.47 (FIG. 4). HRMS m/z: calcd for $C_{38}H_{31}N_2O_2^+$ 547.2380. ([M-Br]+); found 547.2400 (FIG. 5).

Synthesis of Compound TVQ

Figure 6:
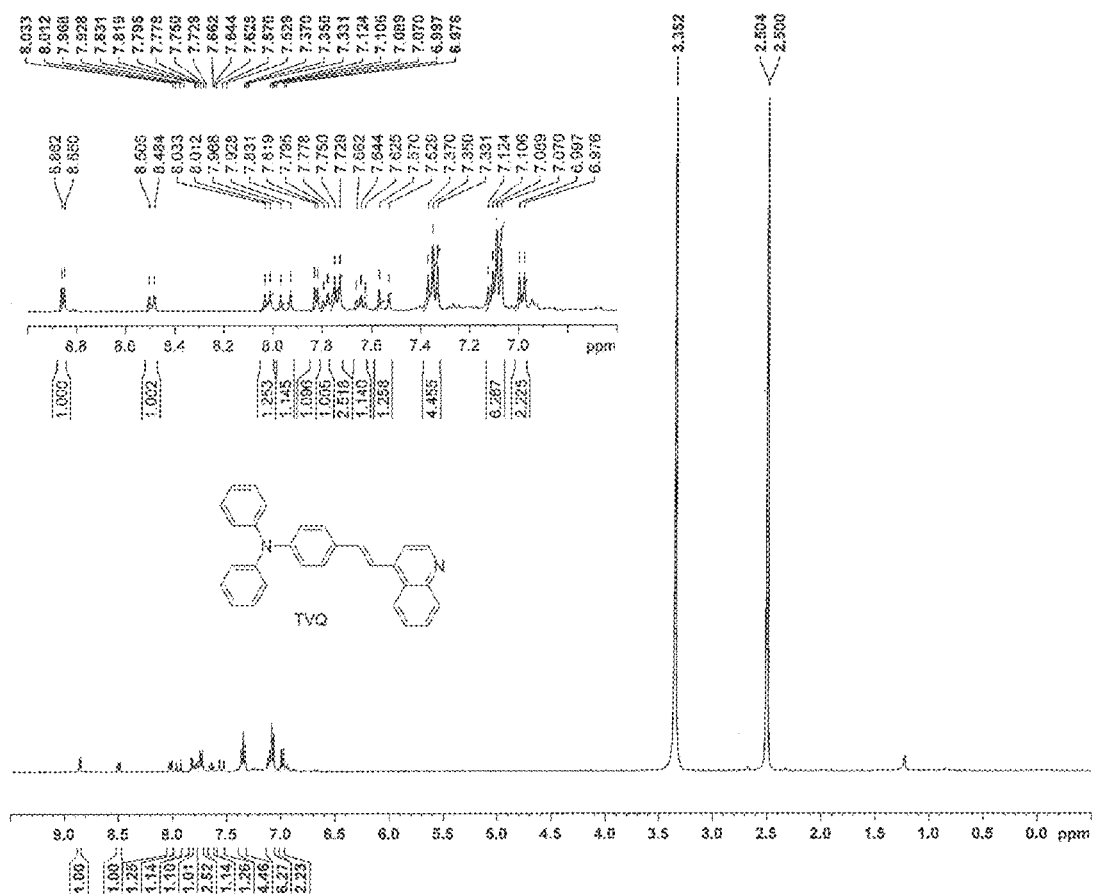
FIG. 6 depicts the $^1$H NMR spectrum of TVQ in DMSO-$d_6$.
Figure 7:
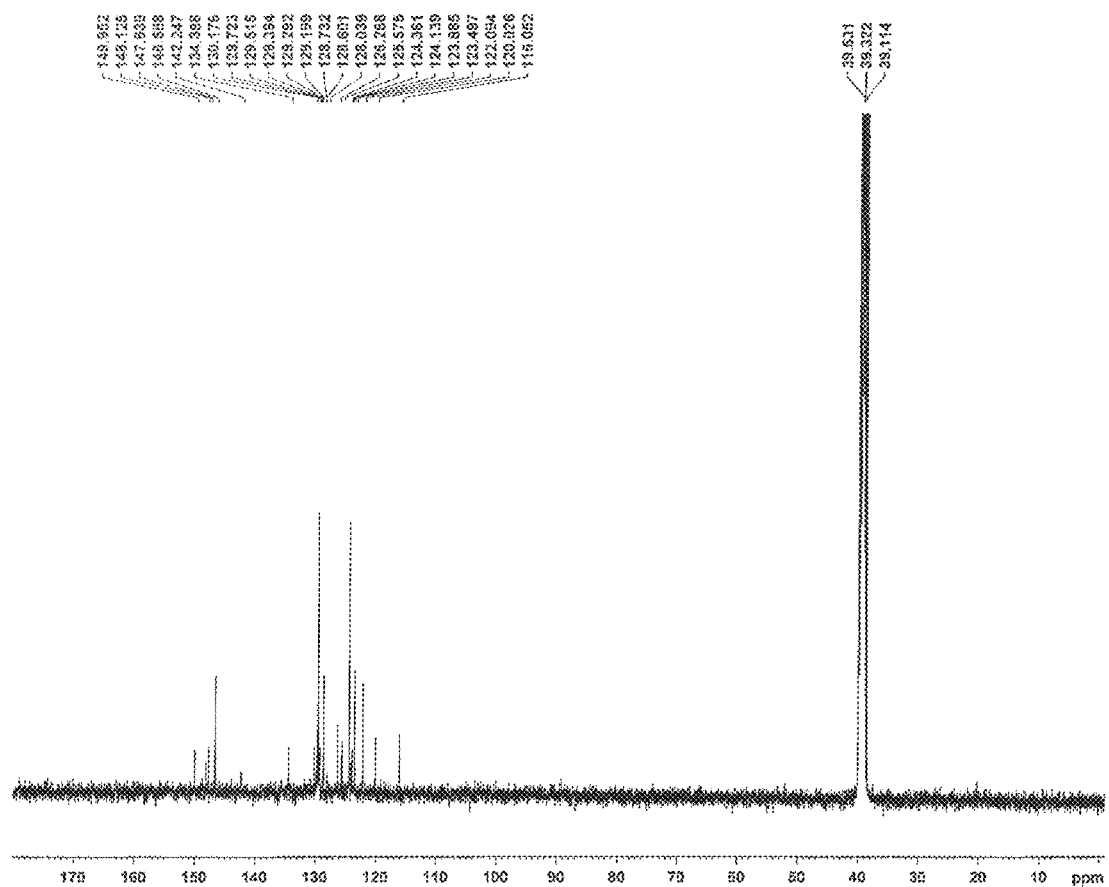
FIG. 7 depicts the $^{13}$C NMR spectrum of TVQ in DMSO-$d_6$.
Figure 8:
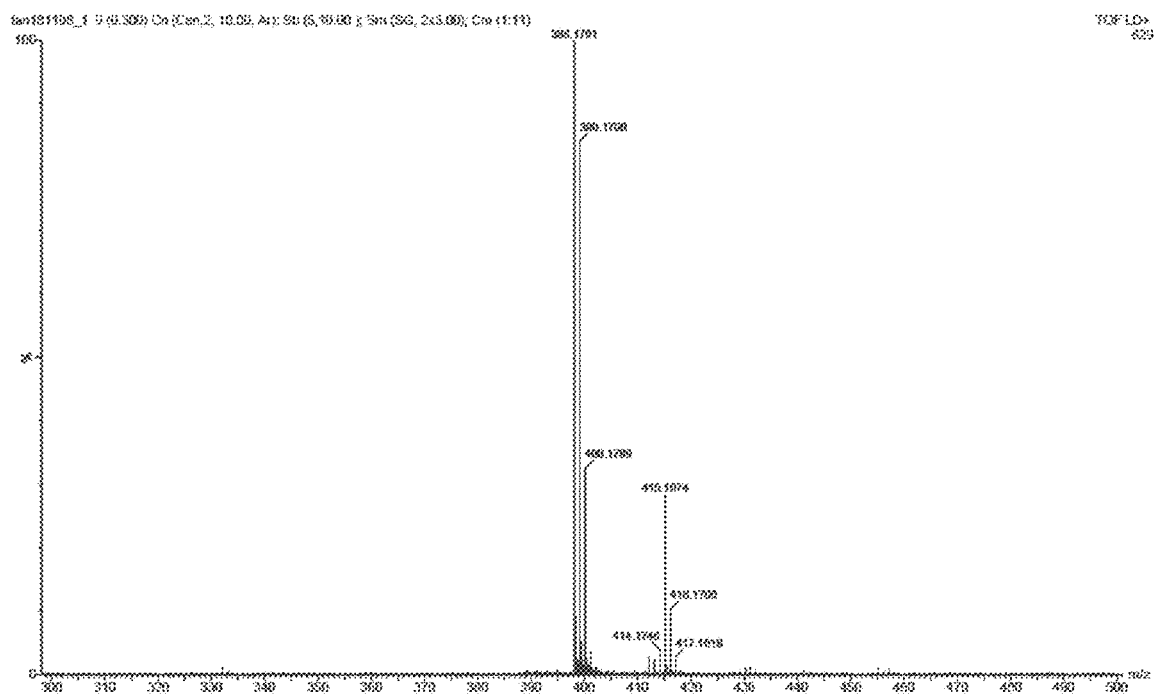
FIG. 8 depicts the HRMS of TVQ.

Compound 5 (0.54 g, 2 mmol) was dissolved in anhydrous DMF (10 mL). Then, compound 3 (0.29 g, 2 mmol) and t-BuOK (0.22 g, 2 mmol) were added. The mixture was stirred at room temperature for 24 h. Then, the residue was purified by flash chromatography directly to give TVQ as a dark yellow solid (0.065 g, 8%). $^1$H NMR (400 MHz, DMSO-$d_6$), δ (ppm): 8.86 (d, J=4.80 Hz, 1H), 8.49 (d, J=8.40 Hz, 1H), 8.02 (d, J=8.40 Hz, 1H), 7.95 (d, J=16.00 Hz, 1H), 7.83 (d, J=4.80 Hz, 1H), 7.79 (d, J=6.80 Hz, 1H), 7.74 (d, J=8.40 Hz, 2H), 7.64 (t, J=7.40 Hz, 1H), 7.55 (d, J=16.40 Hz, 1H), 7.35 (t, J=7.80 Hz, 4H), 7.07-7.12 (m, 6H), 6.99 (d, J=8.40 Hz, 2H) (FIG. 6). $^{13}$C NMR (400 MHz, DMSO-$d_6$), δ (ppm): 149.95, 148.13, 147.64, 146.59, 142.25, 134.39, 130.18, 129.72, 129.52, 129.39, 129.29, 129.20, 128.73, 128.60, 128.04, 126.27, 125.58, 124.36, 124.14, 123.89, 123.50, 122.09, 120.03, 116.05 (FIG. 7). HRMS m/z: calcd for $C_{29}H_{22}N_2$ 398.1783. (ND; found 398.1761 (FIG. 8).

Example 2

Reaction Mechanism and Density Functional Theory Calculation

Figure 9:
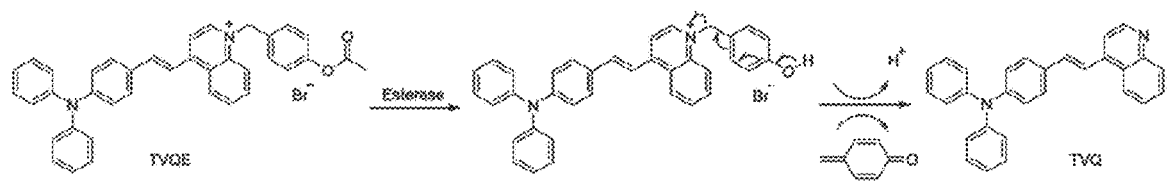
FIG. 9 depicts a proposed reaction mechanism of TVQE towards esterase.
Figures 10A, 10B:
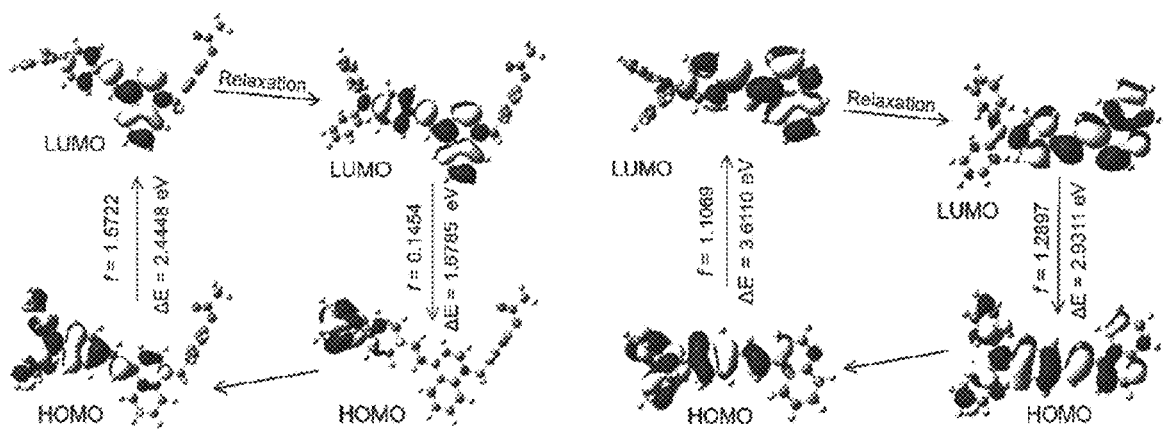
FIGS. 10A-10B depict the frontier orbitals (HOMO and LUMO), energy gaps (ΔE), and transition oscillator strength (f) of the ground and excited states of (FIG. 10A) TVQE and (FIG. 10B) TVQ.

The reaction mechanism of TVQE to esterase is shown in FIG. 9. The acetoxyl group in TVQE was hydrolyzed by esterase and a new molecule was obtained that was not very stable. The newly obtained molecule released a hydrogen ion and benzoquinone before TVQ was generated. Through the density functional theory calculation (FIG. 10), it was predicted that TVQE emits near-infrared fluorescence around 740 nm and TVQ emits blue fluorescence around 420 nm.

Example 3

Photophysical Properties

The absorption and fluorescence (FL) spectra of TVQE and TVQ in different solvents were tested and the results are shown in FIGS. 11A-11D and FIGS. 12A-12D. The corresponding photophysical data are summarized in Table 1.

TABLE 1

Photophysical properties of TVQE

| Solvents | $\lambda_{abs}$ (nm) | $\lambda_{em}$ (nm) | Stokes shift (nm) | $\varepsilon(M^{-1}cm^{-1})$ | $\Phi$ (%) |
|---|---|---|---|---|---|
| Tol | 534 | 659 | 125 | $1.73 \times 10^4$ | 6.6 |
| THF | 522 | 678 | 156 | $1.66 \times 10^4$ | 1.3 |
| EtOH | 548 | 671 | 123 | $1.89 \times 10^4$ | 0.7 |
| Hexane/EtOH = 9/1 | 527 | 656 | 131 | $1.88 \times 10^4$ | 3.0 |

$\lambda_{abs}$ = absorption maximum;
$\lambda_{em}$ = emission maximum;
Abs is absorbance;
$\varepsilon$ is molar absorptivity at maximum absorption wavelength;
$\Phi$ = fluorescence quantum yield.

TVQE showed strong absorbance from 520 nm to 550 nm, and maximum emission from 650 nm to 700 nm, which falls within the near-infrared (NIR) region. TVQ showed maximum absorption of about 400 nm and displayed blue emission from 450 nm to 500 nm. Both TVQE and TVQ possess donor-π-accepter structures. With the increase of solvent polarity, both compounds showed bathochromic shift in FL spectra, due to intramolecular charge transfer effect. In addition, as the electron-withdrawing ability of TVQE's acceptor is much stronger than that of TVQ, TVQE showed a redder shifted emission of nearly 200 nm more than that of TVQ in the same solvent. Furthermore, fluorescence spectra of TVQE in EtOH and EtOH/hexane mixtures with different hexane fraction were shown in FIG. 11A. In pure EtOH, TVQE was weakly emissive with a quantum yield of 0.7%. With the increase of hexane volume content, the FL intensity increased gradually, accompanied with blue-shift in FL maximum from 673 nm to 637 nm, shown in FIG. 11B. When fH=90%, FL intensity reached the maximum with a quantum yield of 3% due to the formation of aggregates, indicating the AIE feature of TVQE. The FL intensity decreased when fH increased to 95%, probably due to the change of the morphology and size of the aggregates.

Figure 11A:
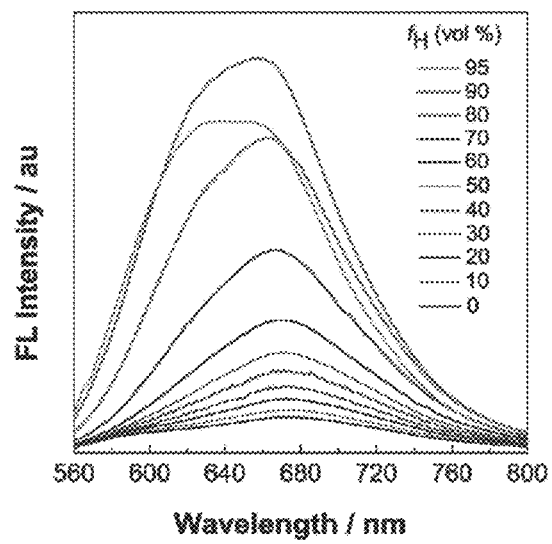
FIGS. 11A-11D depict (FIG. 11A) FL spectra of TVQE in EtOH and EtOH/Hexane mixtures with different Hexane fractions (fH)
Figure 11B:
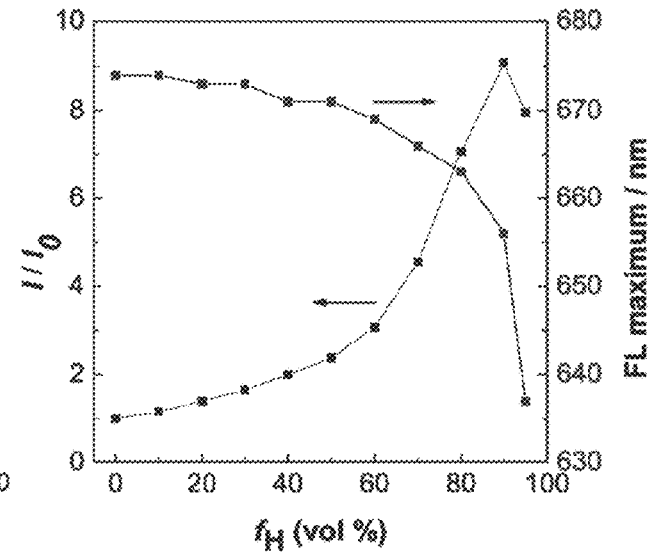
Figure 11C:
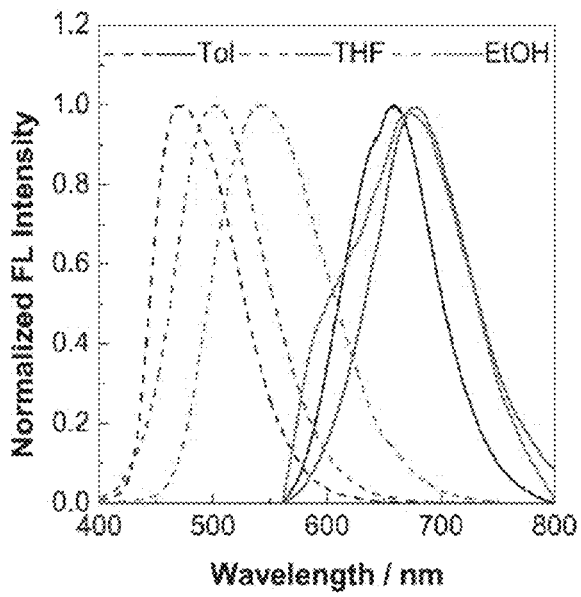
Figure 11D:
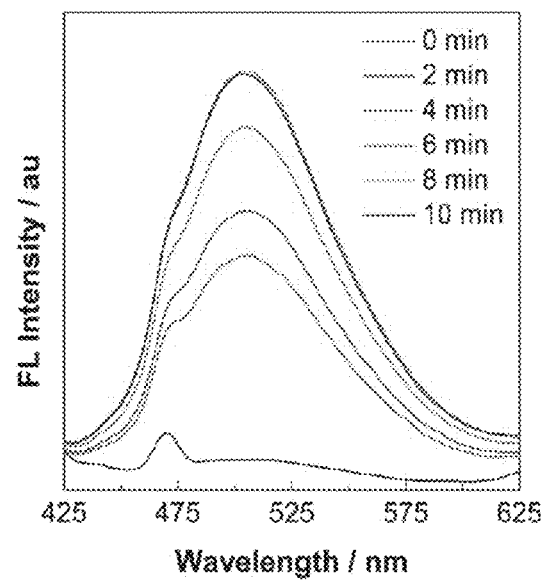
Figure 12A:
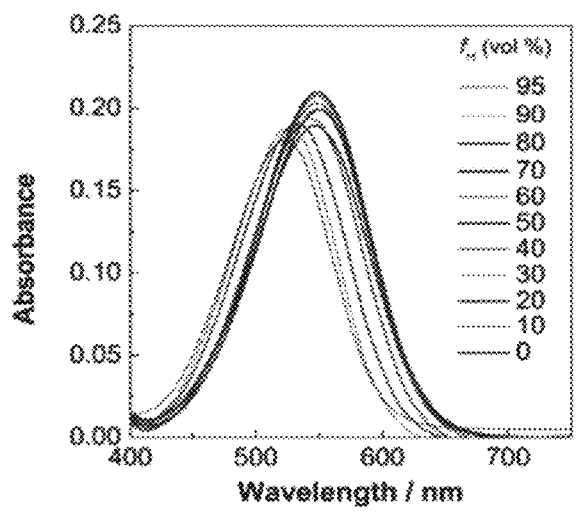
FIGS. 12A-12D depict (FIG. 12A) absorption spectra of TVQE in EtOH and EtOH/Hexane mixtures with different Hexane fractions (fH)
Figure 12B:
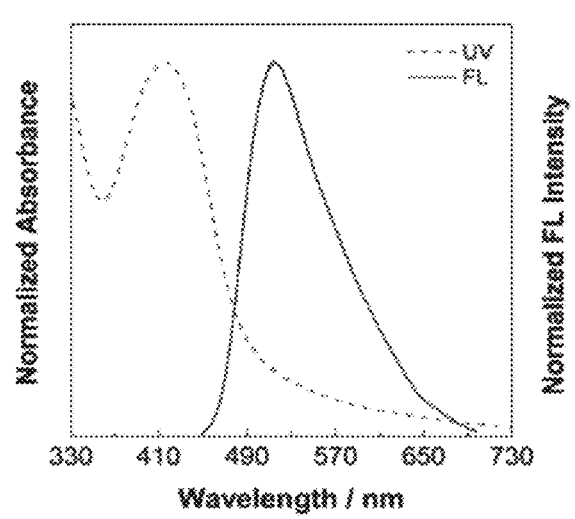
Figure 12C:
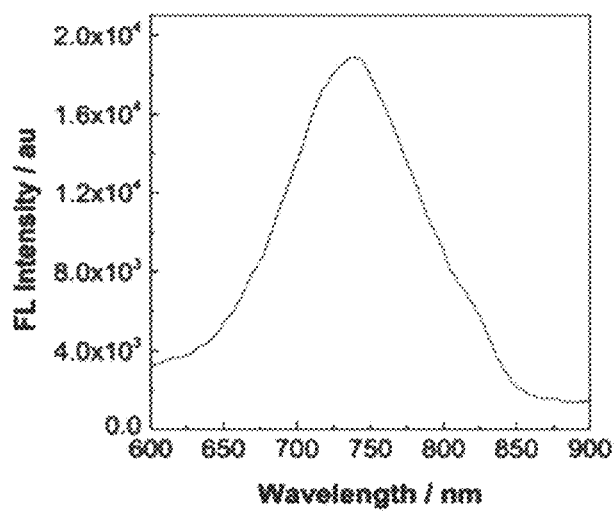
Figure 12D:
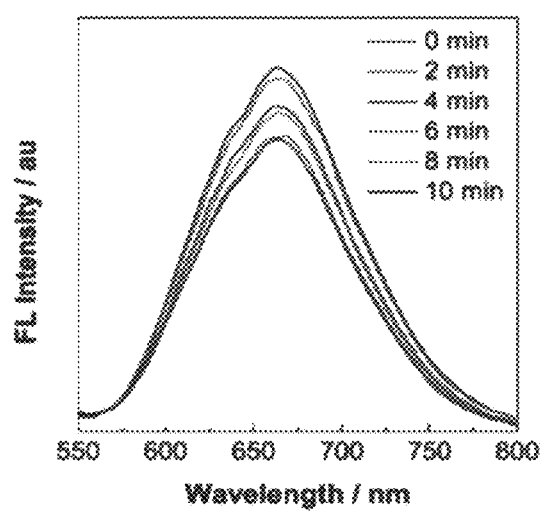

As shown in FIG. 11C, TVQE emitted redder fluorescence of 739 nm in the solid state than in solution with a quantum yield of 2.3%. To get insight into the mechanism of TVQE to esterase, the FL spectra of TVQE treated with active esterase in PBS at room temperature were measured and shown in FIG. 11D. At the beginning, only a weak emission peak at around 700 nm was detected. As treatment time progressed, the fluorescence at about 520 nm increased gradually, which was consistent with the FL spectra of TVQ in PBS, depicted in FIG. 12B. This result indicated that NIR-emissive TVQE could be hydrolyzed to TVQ with blue emission by esterase.

Example 4

Bioimaging

Figure 13:
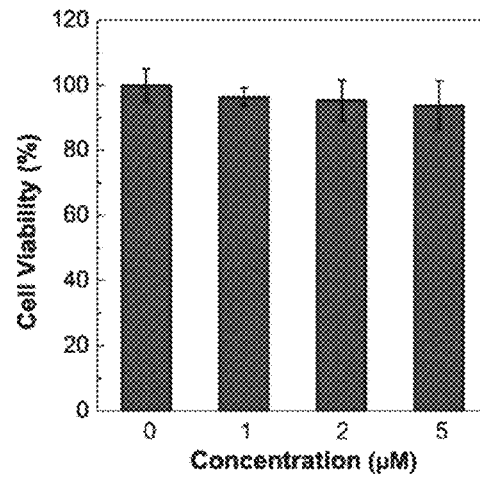
FIG. 13 Viability of HeLa cells after incubation with TVQE at different concentrations for 24 h.
Figure 14A:
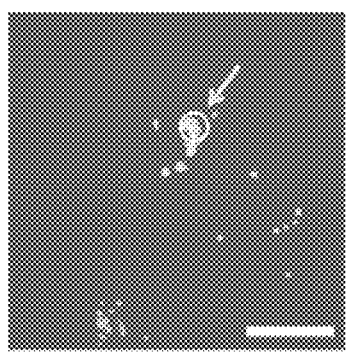
FIGS. 14A-14C depict (FIGS. 14A-14B) images of live HeLa cells stained with 2 μM TVQE and (FIG. 14C) in-situ emission spectra for the circular areas in images depicted in FIGS. 14A-14B (scale bar=20 μm).
Figure 14B:
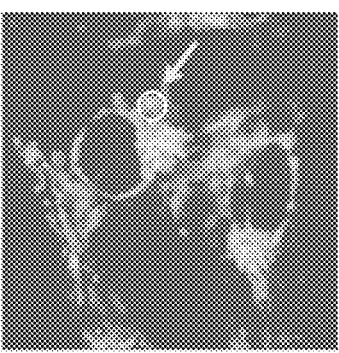
Figure 14C:
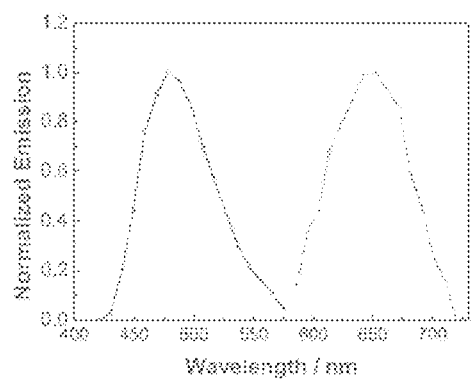
Figure 16A:
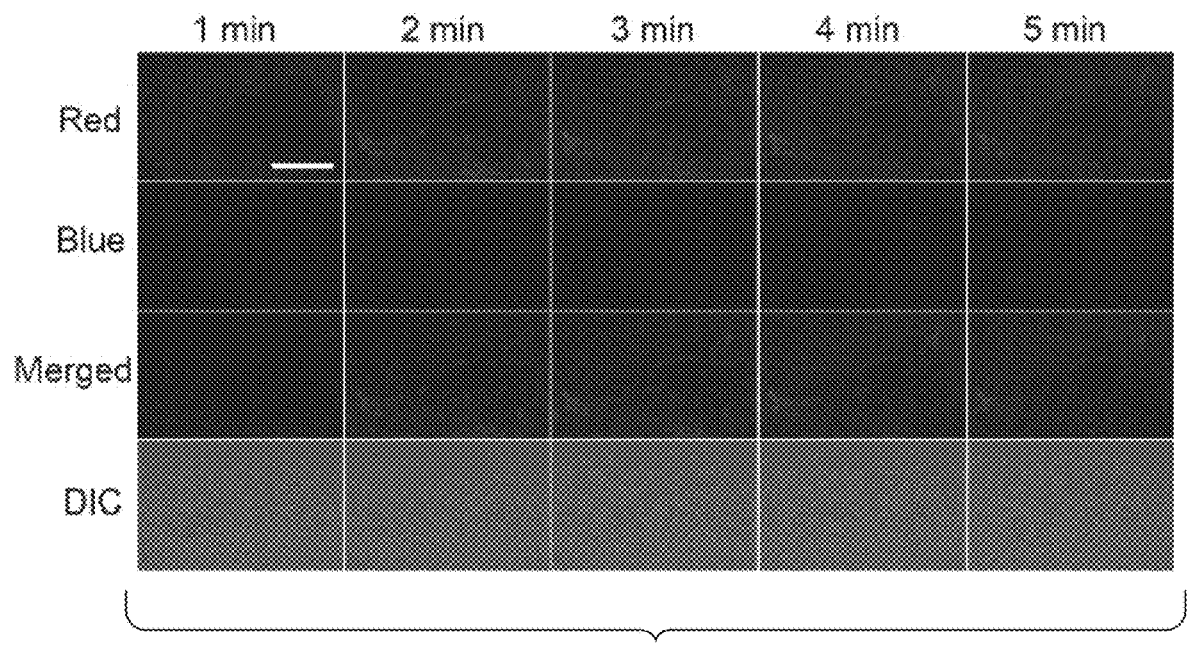
FIGS. 16A-16B depict CLSM images of live HeLa cells stained with 2 μM TVQE at different time points (blue channel: λex=405 nm, λem=420-550 nm; red channel: λex=488 nm, λem=550-700 nm; scale bar=10 μm).
Figure 16B:
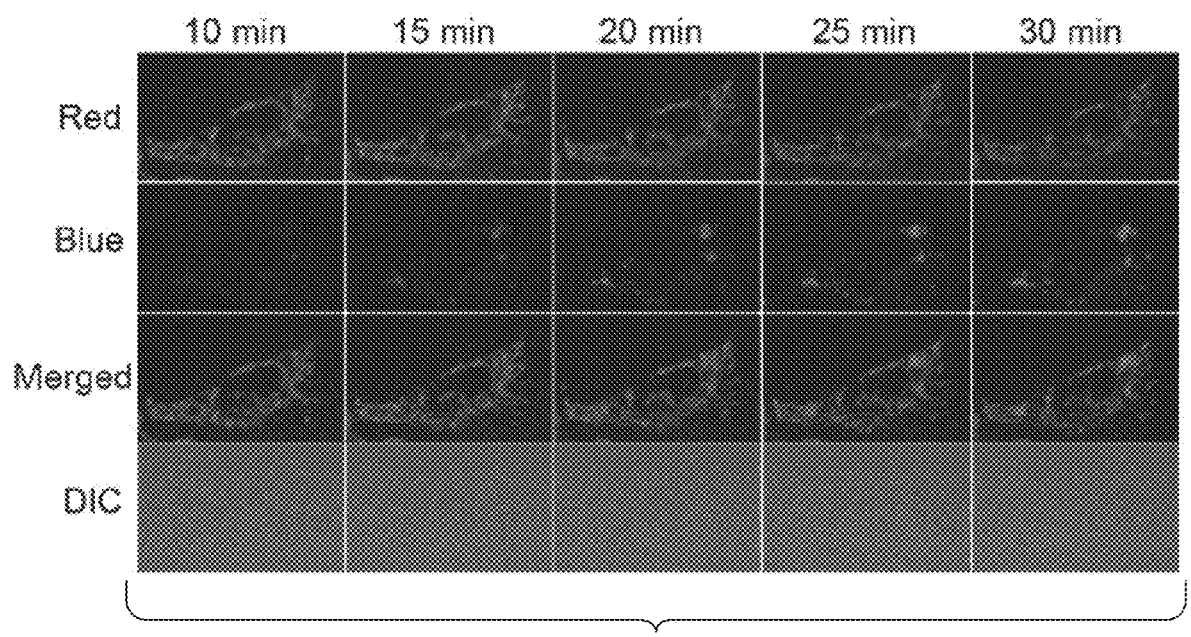
Figure 17A:
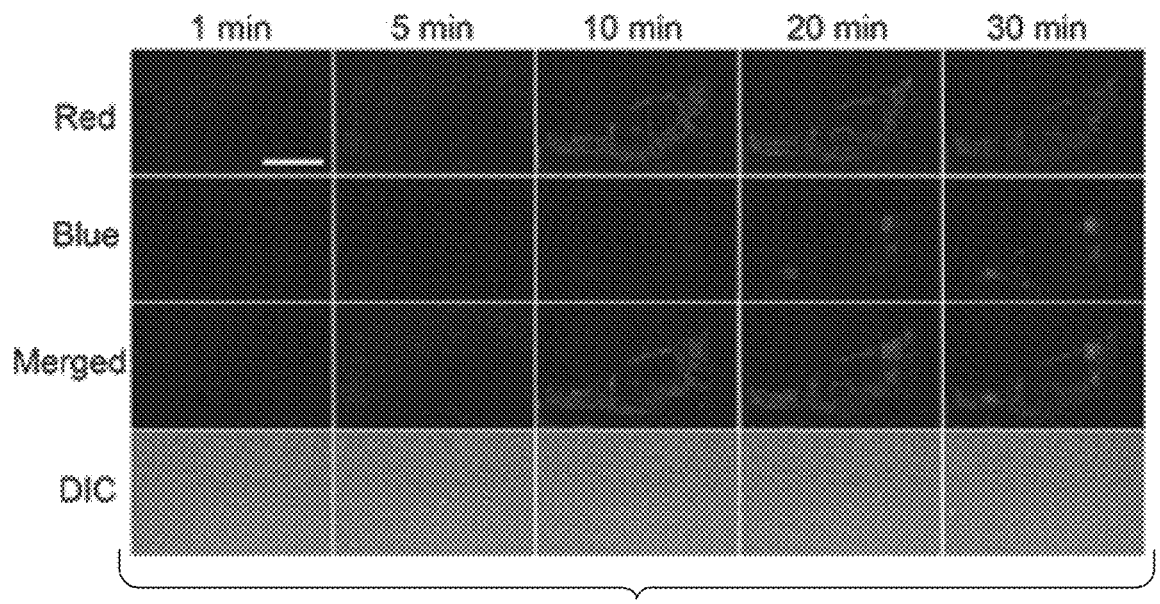
FIGS. 17A-17B depict (FIG. 17A) CLSM images of live HeLa cells stained with 2 μM TVQE at different times (Blue channel: λex=405 nm, λem=420-550 nm; Red channel: λex=488 nm, λem=550-700 nm. Scale bar=10 μm)
Figure 17B:
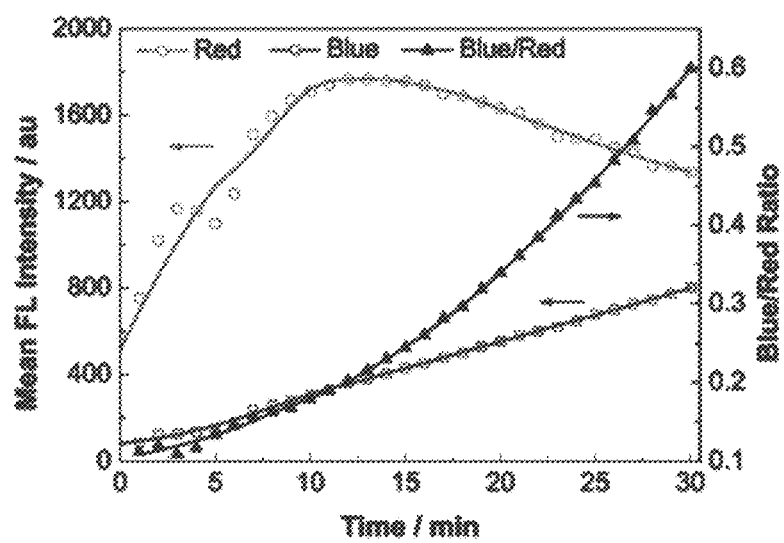

Before bioimaging, the cytotoxicity of TVQE was first studied by standard MTT assay in HeLa cells. As shown in FIG. 13, the viability of HeLa cells was higher than 85% after incubation with TVQE at different concentrations for 24 h, indicating that TVQE is biocompatible with live cells.

Bioimaging experiments were then carried out in live HeLa cells. Based on the spectra imaging function of confocal laser scanning microscope (CLSM), the real color images of live HeLa cells stained with TVQE and in situ emission spectra were obtained (FIGS. 14A-14C and FIG. 15A). It can be seen that TVQE showed both red emission of 650 nm and blue emission of 480 nm inside cells. As designed, TVQE can be hydrolyzed by esterase to provide TVQ. It was speculated that the red emission came from TVQE while the blue emission was from the hydrolysate TVQ.

To verify the speculation, HeLa cells were stained with TVQE and TVQ, respectively, and imaged in dual channels (red and blue channel). As shown in FIG. 15B, strong fluorescence signals were collected in both red and blue channels in TVQE-stained cells, while only blue emission was detected in TVQ-stained cells. The results indicated that TVQE with red emission could be hydrolyzed to blue-emissive TVQ in live cells. In addition, in the red channel of TVQE, clear filamentous structures were observed, which were typical structures of mitochondria. As TVQE includes a cationic moiety, the electrostatic interaction between cationic and mitochondrial membrane potential could drive TVQE to mitochondria. In the blue channel of both TVQE and TVQ, the morphology of lipid droplets was observed, due to a high lipophilicity of TVQ (Calculated log P=8.314).

To further confirm the staining location of TVQE, co-stain experiments with commercialized mitochondrial probe MitoTracker Deep Red FM (MTDR) and lipid-droplet probe Nile Red were performed. As shown in FIG. 15C, the fluorescence signal of TVQE in panels a and e displayed excellent overlap with that of MTDR in panel b and Nile Red in panel f. The co-localization coefficients of TVQE and MTDR or Nile Red were 0.9 and 0.87, respectively, indicating that red-emissive TVQE stained mitochondria, while hydrolyzed TVQE was located in lipid droplets in live cells.

The in situ imaging performance of TVQE in live HeLa cells at different time points was then tracked and investigated (FIGS. 16A-16B and FIGS. 17A-17B). It could be observed that TVQE first stained mitochondria and emitted red fluorescence. Then, after about 5 min, lipid droplets in the blue channel were clearly illuminated. It should be noted that the fluorescence intensity in the red channel increased at the beginning, reached maximum at about 12 min, then decreased gradually. The fluorescence in the blue channel increased with increased time. Hence, the intensity ratios of the blue and red channels increased faster with the progression of time. These results indicated that TVQE first targeted mitochondria due to electrostatic interaction and was then hydrolyzed by esterase with increased time. In addition, the lipophilic hydrolysate tended to accumulate in lipid droplets gradually.

Example 5

Evaluation of Cell Viability

Figure 18:
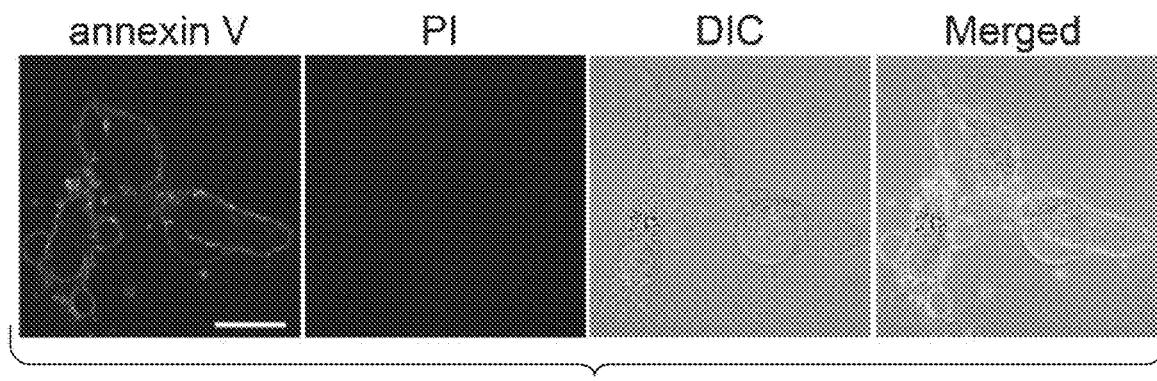
FIG. 18 depicts CLSM images of live HeLa cells treated with 10 mM H$_2$O$_2$ for 1 h and stained with Alexa Fluor 488 annexin V and 1 μM PI for 20 min. Alexa Fluor 488 annexin V: λex=488 nm, λem=500-550 nm; PI: λex=488 nm, λem=600-700 nm. Scale bar=20 μm.

As esterase activity can reflect cell viability, an investigation was conducted to determine whether TVQE could be used to evaluate cell viability. As the esterase possessed high activity in live cells, both blue and red emission signals were strong in live cells, indicating that TVQE was partially hydrolyzed to TVQ by active esterase. In apoptotic cells, the esterase activity decreased, so that the emission in the blue channel was much weaker than that in live cells. When HeLa cells were treated with 10 mM $H_2O_2$ for 1 h and 4.5 h, early and late apoptotic HeLa cells could be clearly and differentially visualized (FIGS. 18 and 19). As shown in FIG. 20A, the blue emission in the late apoptotic stage was weaker than that in the early apoptotic stage. However, nearly no blue-emissive fluorescence signal but strong red emission was detected in dead cells because of the inactivated esterase activity. The different intensity ratios of red and blue channels in live, early apoptotic, late apoptotic and dead cells (FIGS. 20B-20C) indicated that TVQE is able to evaluate different cell viabilities. The fluorescence changes in both blue and red channels of cells in different states were obtained from flow cytometry (Becton Dickinson FACSAria Mu). The numerical values of blue and red channels were associated with the various cell states shown in FIG. 20C. Referring to FIG. 20C, numerical values in the cyan region, e.g., mean fluorescent intensity values around $3.2 \times 10^4$ and 650 in the blue and red channels, respectively correspond to cells that were alive, numerical values in the red region, e.g., mean fluorescence intensity values around $1.4 \times 10^4$ and 780 in the blue and red channels, respectively, correspond to cells in early apoptotic stages, numerical values in the orange region, e.g., mean fluorescence intensity values around 1700 and 4200 in the blue and red channels, respectively, correspond to cells in the late apoptotic stages, and numerical values in the green region, e.g., mean fluorescence intensity values around 780 and $1.5 \times 10^4$ in the blue and red channels, respectively, correspond to cells that were dead.

Flow cytometry is a widely used tool for statistical analysis. It has different laser sources and is suitable for simultaneous detection of multichannel fluorescence signals. A flow cytometry assay was performed to monitor the fluorescence changes in both red and blue channels of cells at different physiological stages. Live cells exhibited strong intensity in the blue channel and relatively weaker signals in the red channel. Compared with live cells, the blue emission in early apoptotic cells was a little weaker. Late apoptotic and dead cells showed much stronger signals in the red channel, but much weaker blue emission than that in live and early apoptotic cells. The red emission in dead cells was stronger in comparison with late apoptotic cells. The results demonstrated that TVQE is able to statistically differentiate live, early apoptotic, late apoptotic and dead cells by flow cytometry.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:
1. A fluorescent probe, comprising a compound having the following structural formula:

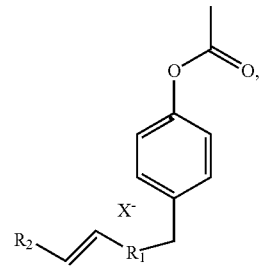

wherein $X^-$ is selected from the group consisting of $Br^-$, $I^-$, $PF_6^-$, and $ClO_4^-$;
$R_1$ is selected from the group consisting of

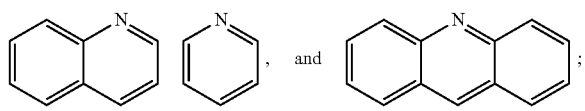

and
$R_2$ is selected from the group consisting of

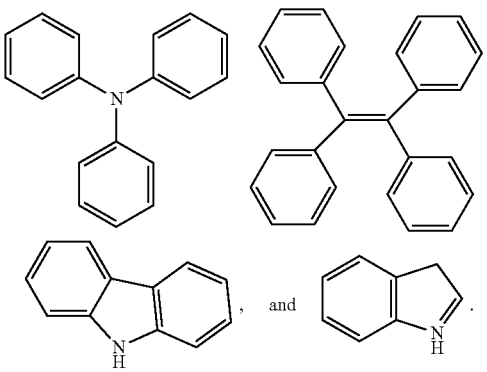

2. The fluorescent probe of claim 1, wherein the compound is:

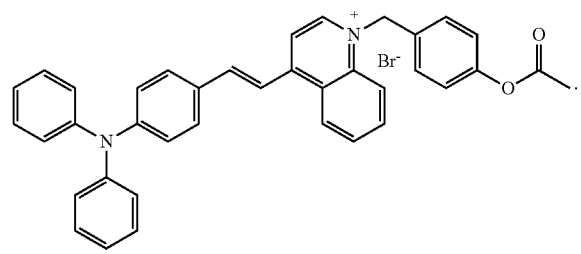

TVQE

3. A method of cellular imaging, comprising:
contacting a target cell with the compound of claim 1, and
identifying at least one cellular target of interest using an imaging method.

4. The method of claim 3, wherein the imaging method is selected from the group consisting of fluorescence microscopy and confocal laser scanning microscopy.

5. The method of claim 3, wherein the target cell is a live cell.

6. The method of claim 3, wherein the target cell is a cancer cell.

7. The method of claim 3, wherein the at least one target of interest comprises at least one of a mitochondrion and a lipid droplet.

8. The method of claim 3, wherein the at least one target of interest comprises a mitochondrion and a lipid droplet.

9. A method of determining viability of a cell, comprising:
contacting a target cell with the compound of claim 1, and
detecting esterase activity using an imaging method, wherein
a change of emission from red to blue indicates hydrolysis of the compound by esterase, and
an intensity ratio of a red emission and a blue emission indicates viability of the target cell.

10. The method of claim 9, wherein the imaging method is selected from the group consisting of fluorescence microscopy and confocal laser scanning microscopy.

11. The method of claim 9, wherein the target cell is a cancer cell.

12. The method of claim 11, wherein the intensity ratio indicates a cell state selected from the group consisting of live, early apoptotic, late apoptotic, and dead.

13. A fluorescent probe comprising the following compound:

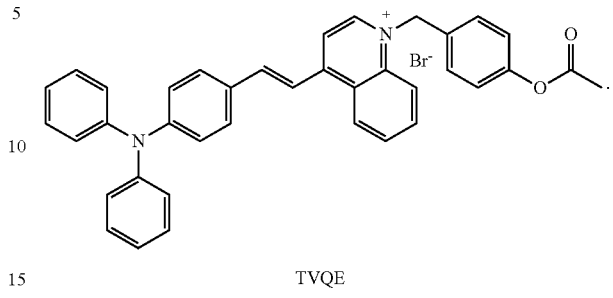

TVQE

14. A method of cellular imaging, comprising:
contacting a target cell with the compound of claim 13, and
identifying at least one cellular target of interest using an imaging method.

15. The method of claim 14, wherein the imaging method is selected from the group consisting of fluorescence microscopy and confocal laser scanning microscopy.

16. The method of claim 14, wherein the target cell is a live cell.

17. The method of claim 14, wherein the target cell is a cancer cell.

18. The method of claim 14, wherein the at least one target of interest comprises at least one of a mitochondrion and a lipid droplet.

19. The method of claim 14, wherein the at least one target of interest comprises a mitochondrion and a lipid droplet.

* * * * *